US006596667B2

(12) United States Patent
Bellussi et al.

(10) Patent No.: US 6,596,667 B2
(45) Date of Patent: Jul. 22, 2003

(54) SUPPORTED COBALT-BASED CATALYST

(75) Inventors: Giuseppe Bellussi, Piacenza (IT); Roberto Zennaro, Venezia (IT); Vincenzo Piccolo, Paullo (IT); Enrico Radaelli, Brugherio (IT); Magalie Roy-Auberger, Rueil-Malmaison (FR)

(73) Assignees: Eni S.p.A., Rome (IT); AGIP Petroli S.p.A., Rome (IT); Institut Francais du Petrole, Rueil-Malmaison (FR); Enitecnologie S.p.A., San Donato Milanese (IT)

( * ) Notice: Subject to any disclaimer, the term of this patent is extended or adjusted under 35 U.S.C. 154(b) by 46 days.

(21) Appl. No.: 09/795,105

(22) Filed: Mar. 1, 2001

(65) Prior Publication Data

US 2001/0041750 A1 Nov. 15, 2001

(30) Foreign Application Priority Data

Mar. 2, 2000 (IT) ....................... MI2000A0409

(51) Int. Cl.⁷ ..................... B01J 23/40; B01J 23/42; B01J 23/56
(52) U.S. Cl. ................ 502/332; 502/327; 502/355; 502/415; 502/439
(58) Field of Search ................. 502/326, 327, 502/332, 439, 260, 415, 355

(56) References Cited

U.S. PATENT DOCUMENTS

| 3,853,789 A | * | 12/1974 | Warthen et al. ............ 252/463 |
| 3,909,455 A | | 9/1975 | Rainer et al. |
| 3,929,682 A | * | 12/1975 | Kuhrt et al. ............ 252/466 PT |
| 4,200,552 A | * | 4/1980 | Noguchi et al. ......... 252/466 PT |
| 4,229,234 A | * | 10/1980 | Krutenat et al. ............ 148/105 |
| 4,312,791 A | * | 1/1982 | Antos ..................... 252/466 B |
| 4,324,645 A | * | 4/1982 | Angevine et al. ............ 208/50 |
| 4,413,064 A | | 11/1983 | Beuther et al. |
| 4,923,843 A | * | 5/1990 | Saforo et al. .............. 502/415 |
| 5,166,121 A | * | 11/1992 | Khare et al. ............... 502/225 |
| 5,229,347 A | * | 7/1993 | Prada et al. ............... 502/221 |
| 5,244,648 A | * | 9/1993 | Dupin et al. ............... 423/626 |
| 5,266,548 A | * | 11/1993 | Koradia et al. ............. 502/439 |
| 5,286,697 A | * | 2/1994 | Van Den Brink et al. .. 502/257 |
| 5,427,995 A | * | 6/1995 | Ziebarth et al. ............ 502/411 |
| 5,545,602 A | * | 8/1996 | Nelson et al. .............. 502/314 |
| 5,637,547 A | * | 6/1997 | Chopin et al. .............. 502/415 |
| 5,639,798 A | | 6/1997 | Wilson et al. |
| 6,033,556 A | * | 3/2000 | Didillon et al. ............. 208/253 |
| 6,043,187 A | * | 3/2000 | Harle et al. ................. 502/313 |
| 6,075,062 A | * | 6/2000 | Zennaro et al. ............ 518/715 |
| 6,121,190 A | * | 9/2000 | Zennaro et al. ............ 502/326 |
| 6,130,360 A | * | 10/2000 | Bottcher et al. ............ 568/861 |
| 6,207,611 B1 | * | 3/2001 | Sun et al. ................... 502/325 |
| 6,218,335 B1 | * | 4/2001 | Okada et al. ............... 502/340 |
| 6,248,924 B1 | * | 6/2001 | Ruhl et al. .................. 564/450 |
| 6,262,132 B1 | * | 7/2001 | Singleton et al. ........... 518/715 |

* cited by examiner

Primary Examiner—Stanley S. Silverman
Assistant Examiner—Cam N. Nguyen
(74) Attorney, Agent, or Firm—Oblon, Spivak, McClelland, Maier & Neustadt, P.C.

(57) ABSTRACT

A supported cobalt-based catalyst characterized in that the carrier has an average particle diameter, measured by means of Coulter LS230, ranging from 70 to 250 μm, a surface area higher than 175 m²/g and a pore volume higher than 0.35 cm³/g, measured with the B.E.T. method. The catalyst is useful in the Fischer-Tropsch reaction.

6 Claims, 3 Drawing Sheets

SUPPORTED COBALT-BASED CATALYST

Figure 1:
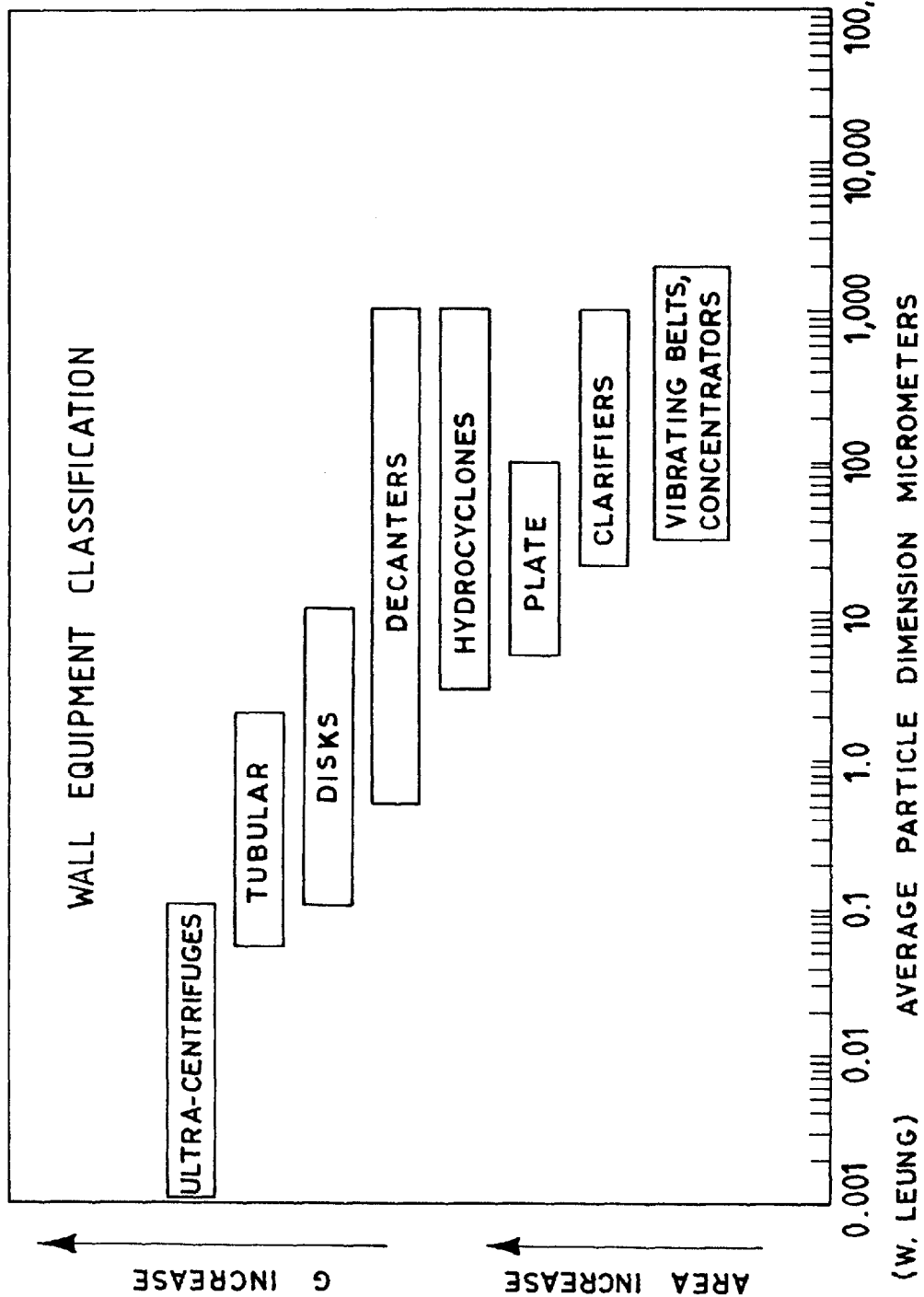

The present invention relates to a supported Cobalt-based catalyst, which can be used in the Fischer-Tropsch reaction in a gas-liquid-solid fluidized reactor.

DESCRIPTION OF THE BACKGROUND

The activity of Fischer-Tropsch catalysts can be influenced by all physical factors which affect the mass transfer rate of the reagents and products, between the various phases and heat transfer. As a result, it can be observed that under diffusive regime conditions, there is not only a lower reaction rate but also a change in the selectivity of the various products, jeopardizing the performance of the whole process both from a quantitative and qualitative point of view.

In a catalytic reaction, the transfer processes of material and heat between fluid and catalyst depend on the fluid-dynamic regime to which the reagents and reaction products are subjected and on the geometry of the reactor, i.e. the type of reactor solution adopted.

In the Fischer-Tropsch synthesis fixed bed reactors, entrainment reactors, fluidized bed reactors can be used, as described in the U.S. Pat. No. 4,670,472 (Dyer et al.). More recently gas-liquid-solid (slurry bubble column) fluidized systems are preferred to other reactor solutions. The flow-rates of the fluids in these solutions must be such as to guarantee a more or less homogeneous suspension of the catalyst in the entire reaction volume and to facilitate the removal of the heat produced by the exothermic reaction, improving the heat exchange between reaction zone and a suitable exchanger introduced into the column. As far as the catalyst is concerned, the solid particles must have sufficiently large dimensions as to be easily separated from the liquid products, but sufficiently small as to minimize intra-particle diffusion limitations.

Limitations to transport processes (of matter and/or heat) can be subdivided into external (or inter-particle) diffusion regime and internal (or intra-particle) diffusion regime. The entity of the phenomenon linked to external diffusion depends on the fluido-dynamics and geometry of the system, i.e. on the rate and characteristics of the reagent fluid and interphase surface area (form and dimensions of the catalyst particles). Internal diffusion phenomena, on the other hand, depend on the chemical and morphological structure of the catalyst (pore dimensions, surface area, density of the active sites) and on the molecular dimensions of the species in question.

Multiphase reactors of the slurry type generally use small catalyst particles (20–150 $\mu$m) which do not give internal diffusion problems but can be subject to external mass transfer limitations owing to the low diffusion of the gases in the hydrocarbon liquid and relatively low fluid rate. On the contrary, the relatively high thermal conductivity of the liquid allows external heat transfer limitations to be ignored (J. M. Smith, "Chemical Engineering Kinetics", McGraw Hill Int. D., 1988, chap. 10, page 415).

Internal transport phenomena, on the other hand, are linked to the morphological parameters of the porous material used as carrier of the active phase, which determine the diffusion capacity inside the catalyst particle. The effect of intra-particle transport limitations is to generate a negative concentration gradient of the reagents inside the catalyst particle which, as final effect, causes a drop in the reaction rate.

In the same way it is possible to observe temperature gradients which, due to an exothermic reaction, such as the Fischer-Tropsch synthesis, create a temperature rise towards the center of the catalyst particle increasing its reaction rate, thus, with an effect contrary to mass transfer, favoring the selectivity to light hydrocarbons. Also in the case of reactions with a decrease in the number of moles, total pressure gradients are produced, capable of creating reagent streams towards the particle center. While on the one hand, this phenomenon increases the diffusion of the reagents towards the inside of the catalyst, on the other hand it delays the diffusion of the reaction products towards the outside.

In a multiphase reaction such as the Fischer-Tropsch synthesis, the transport processes of the reagents and products are conditioned by the presence of the hydrocarbon liquid produced. More specifically, the different diffusivities of the reagents (CO, $H_2$) in the hydrocarbon liquid, approximately a $10^3$–$10^4$ factor lower with respect to the diffusivities in the gas, create low concentrations of CO towards the center of the particle with a consequent progressive rise in the $H_2$/CO ratio inside the catalyst. This condition favors the formation of light hydrocarbons and secondary reactions of the main products. From studies presented in literature in this field, it can be observed how, for catalysts based on differently supported cobalt used in the Fischer-Tropsch synthesis, it is possible to neglect internal diffusional limitations by operating with particles having a diameter of less than 200 $\mu$m) (Iglesia, et al., Computer-aided Design of Catalysts, ED. Becker-Pereira, 1993, chap. 7).

In more general terms, for any catalytic reaction, internal transport phenomena become less important with the decrease in the catalyst particle dimension. For example for fluidized-bed or slurry applications, intra-particle heat transport limitations are generally negligible (J. M. Smith, "Chemical Engineering Kinetics", McGraw-Hill Int. D., 1988, chap. 11, page 451).

The ideal case in which there can be a total absence of mass and heat transport limitations is represented by homogeneous catalysts. These homogeneous systems however are not applied in many processes, owing to the difficulties and costs relating to the separation of the catalyst from the reaction medium. These costs, in fact, are often higher than the benefits deriving from the absence of diffusion limitations.

The catalyst particle dimensions are therefore of fundamental importance and must be sufficiently small so as to avoid constrictions to the mass and heat transport due to internal diffusion limitations and at the same time sufficiently large as to be easily separable from the suspension liquid.

The use of a slurry bubble column reactor (SBCR) in a gas-liquid-solid multiphase system in the Fischer-Tropsch synthesis is among the preferred reactor solutions. More specifically, in an SBCR, the catalyst is suspended in a hydrocarbon liquid, often the reaction product itself. The synthesis gas, consisting of CO, $H_2$, $N_2$, $CO_2$, is fed by means of a suitable distributor capable of generating gas bubbles dispersed inside the suspension. The gas bubbles migrate upwards towards the slurry, being subjected to coalescence and breakage phenomena. In this way a wide distribution of the bubble diameters is created (3–80 mm), which determines the mixing and distribution of the catalyst inside the bubble column. The effectiveness of the mixing, and therefore the dispersion degree of the solid in the liquid, is mainly linked to the entrainment of the large gas bubbles (20–80 mm) with a rate of about 1–2 m/s.

The gaseous products are sent towards the top of the reactor and then processed externally, whereas the liquid products are recovered by filtration of the catalyst.

In spite of the advantages acknowledged in the use of an SBCR in the Fischer-Tropsch reaction (see references present in U.S. Pat. No. 5,939,350, col. 2) the aspects relating to the filtration are a critical point for the use of the whole process, owing to the reduced average particle dimensions of the solid used. To facilitate the filtration operations, it is therefore necessary to operate with catalyst particles having a sufficiently large diameter. The highest limit of the average particle diameter obviously depends on the catalytic performances obtained, which, as already mentioned, must not be affected by limitations of the diffusional type, capable of reducing the effectiveness of the catalyst with respect to what would be obtained in kinetic regime.

SUMMARY OF THE INVENTION

The innovative element of the present invention relates to the identification of a carrier with suitable morphological characteristics as to make it appropriate for application in a gas-liquid-solid fluidized reactor (SBCR) capable of simplifying the liquid/solid separation phase as a result of the favorable particle dimension of the carrier itself, and not negatively influencing the effectiveness of the catalyst, due to limitations in the mass and heat transport.

In accordance with this, the present invention relates to a supported cobalt-based catalyst characterized in that the carrier, preferably consisting of at least 80% of aluminum oxide, has an average particle diameter, measured by means of Coulter LS230, ranging from 70 to 250 $\mu$m, preferably from 120 to 180 $\mu$m, a surface area higher than 175 m$^2$/g, preferably from 185 m$^2$/g to 210 m$^2$/g, and a pore volume higher than 0.35 cm$^3$/g, preferably higher than 0.40 cm$^3$/g, measured with the B.E.T. (Brunauer, Emmett, Teller) method.

DETAILED DESCRIPTION OF THE PREFERRED EMBODIMENTS

In the preferred embodiment, the carrier mainly consists (>80%) of aluminum oxide in any phase composition selected from: eta, gamma, delta, theta, alpha and their mixtures, in the presence of or without a structural stability promoter of the carrier itself such as Si, Zr, Ta, Zn, Sn, Mn, Ba, Ca, La, Ce. The addition of these elements or their mixtures is carried out according to the usual techniques of the known art by the use of precursors such as nitrates, oxalates, tartrates, halides, alkoxides. For example, additives such as Si, Ba, Ce, La, Ca reduce sintering and delay the phase transformation of the alumina without influencing the porosimetric characteristics of the starting alumina itself (R. J. Ferrauto, C. H. Bartholomew in "Fundamentals of Industrial Catalytic Process", Blackie Academic & professional, 1997).

The active phase of this group of catalysts should mainly consist (>80%) of Cobalt in the presence of or without an activity promoter with a differing effect on the catalytic performances as described in the state of the art (see for example B. Jager, R. Espinoza in "Catalysis Today", 23, 1995, 21–22). For example promoters such as K, Na, Mg, Sr, Cu, Mo, Ta, W and metals of the VIII group essentially increase the activity. Ru, Zr, rare earth oxides (REO), Ti increase the selectivity to high molecular weight hydrocarbons. Ru, REO, Re, Hf, Ce, U, Th favor the regenerability of cobalt catalysts.

The supported cobalt-based catalysts of the present invention are prepared according to the most common techniques known to experts in the field, such as, for example, ion exchange, incipient wetness impregnation, precipitation of cobalt, co-precipitation of cobalt and promoter, gelation and mechanical mixing. In the preferred embodiment the catalysts are prepared according to the incipient wetness impregnation technique.

A further object of the present invention relates to a Fischer-Tropsch process which comprises the reaction of CO and $H_2$, optionally diluted with $CO_2$ and/or $N_2$, to give prevalently $C_{5+}$ hydrocarbons, characterized in that it is carried out in the presence of the catalyst of the present invention described above.

The Fischer-Tropsch process is a well known process and the reaction conditions are described in literature. For example, the temperatures can vary from 170° C. to 400° C., preferably from 180° C. to 250° C., whereas the pressures can vary from 1 to 100 bars, preferably from 15 to 40 bars. The CO/$H_2$ ratio can vary from 0.5/1 to 4/1, preferably from 1.7/1 to 2.5/1, the stoichiometric ratio (more or less 3%) being preferred. The catalyst of the present invention is preferably used in a slurry bubble reactor with hourly space velocities of the gas ranging from 4000 to 20000.

The following examples are provided for a better understanding of the present invention.

EXAMPLES

In the examples of the present invention, catalysts are used, obtained as described in EP-A-857,513 in relation to the preparation of the catalytic precursor containing cobalt alone. In the experimental examples, gamma-alumina having the characteristics indicated in Table 1, was used as carrier.

TABLE 1

Morphological characteristics of alumina-based carriers.

| CARRIER (Al$_2$O$_3$) | A | B | C | D | E |
|---|---|---|---|---|---|
| crystalline phase | gamma | gamma | gamma | gamma | gamma |
| surface area (m$^2$/g) | 170 | 175 | 192 | 120 | 205 |
| specific pore volume (cm$^3$/g) | 0.43 | 0.35 | 0.48 | 0.25 | 0.53 |
| average particle distribution ($\mu$m) | 60 | 65 | 165 | 165 | 165 |
| Catalyst abbreviation | CAT-A | CAT-B | CAT-C | CAT-D | CAT-E |

All the catalysts indicated in the examples consist of 14% by weight of cobalt, prepared by means of the incipient wetness technique, known to experts in the field, of a carrier based on alumina with an aqueous solution of cobalt nitrate, Co(NO$_3$)$_2$.6H$_2$O. The catalysts were used in a reactivity test in a 2-liter CSTR reactor (Continuous Stirred Tank Reactor), fed in continuous with a mixture of CO and $H_2$ under the conditions indicated below:

TABLE 2

Operating conditions of the catalytic tests.

| Reaction temperature: | 230–240° C. |
|---|---|
| Total pressure: | 21 abs. bars |
| H$_2$/CO ratio: | 2/1 |
| Space velocity: | 1.3–3.0 Nl/g$_{cat}$/h |

Description of the Catalytic Tests

The catalyst is charged, in the pre-selected quantities, into a fixed bed tubular reactor and activated by means of reduction in hydrogen (2,000 Nl/h/l$_{cat}$) and nitrogen (1,000

Nl/h/l$_{cat}$) at a temperature ranging from 320–450° C. and a pressure of 1 bar for 16 hours. The catalyst thus activated is transferred, in the absence of air and in a stream of nitrogen, inside a stirred autoclave (CSTR reactor) containing n-paraffin fluidified at a temperature of 130° C. in the presence of a stream of nitrogen 30 Nl/h. The blade stirring system is subsequently activated at a rate of 1,000 rpm and maintained under these conditions for 16 hours. During this phase the system is brought to the final operating pressure of 20–30 bars. At the end of this phase the reagent mixture consisting of $H_2$ and CO is introduced in a stoichiometric ratio of 2:1 by the progressive entry of CO—$H_2$ and reduction of the $N_2$ feeding. The operation is completed within a time range of 4 hours at a temperature of 130° C. as indicated in Table 3.

TABLE 3

Feeding conditions in activation phase.

| Time (hours) | $H_2$ Flow-rate (Nl/h/l$_{cat}$) | CO Flow-rate (Nl/h/l$_{cat}$) | $N_2$ Flow-rate (Nl/h/l$_{cat}$) |
|---|---|---|---|
| 0 | 330 | 165 | 1170 |
| 2 | 770 | 385 | 500 |
| 4 | 1117 | 558 | 0 |

At the end of this activation phase, the system proves to be totally without gaseous diluent ($N_2$) and under the conditions of pressure, space velocity, $H_2$/CO ratio indicated in Table 2. The temperature is then raised to the reaction temperature in about 15 hours. The level of the liquid inside the reactor is automatically kept constant by means of a regulation system based on the pressure difference between the top and bottom of the autoclave. The waxes produced are removed from the reactor by means of a filtrating system, capable of withholding the catalyst, and stored at a temperature of 150° C. The effluent gas from the reactor passes through two traps in series at a respective temperature of 30° C. and 0° C. The gas leaving the traps passes through a meter and a subsequent sampling system for gas-chromatographic analysis. The solid and liquid effluents are analyzed with a suitable gas-chromatographic apparatus for the total quantification.

In order to normalize the catalytic activity data of the various tests, with respect to the actual cobalt content, the yield to products containing carbon (hydrocarbons and $CO_2$) is used as comparison parameter, normalized for the actual moles of cobalt present in the catalyst and the time unit: defined as CoTY (Cobalt-Time Yield) converted CO moles/ total Co moles/hour.

Example 1 Comparative 1

Catalyst CAT-A supported on $Al_2O_3$ of the type A characterized by the following morphological parameters: gamma crystalline phase, surface area equal to 170 m$^2$/g, specific pore volume of 0.43 cm$^3$/g, average particle distribution of 60 μm.

The catalytic activity tests carried out with the above catalyst can be considered as being the basic case for which it is possible to obtain intrinsic catalytic activity data ignoring limitations of a diffusional nature. The catalytic activity data obtained at two different temperatures are indicated in Table 4.

Example 2 Comparative 2

Catalyst CAT-B supported on $Al_2O_3$ of the type B characterized by the following morphological parameters: gamma crystalline phase, surface area equal to 175 m$^2$/g, specific pore volume of 0.35 cm$^3$/g, average particle distribution of 65 μm. The data of the catalytic activity tests obtained at a different GHSV and $H_2$/CO ratio are indicated in Table 5.

Example 3 Comparative 3

Catalyst CAT-B supported on $Al_2O_3$ of the type B characterized by the following morphological parameters: gamma crystalline phase, surface area equal to 175 m$^2$/g, specific pore volume of 0.35 cm$^3$/g, average particle distribution of 65 μm.

The catalytic activity tests differ from example 2 in the different operating conditions and quantity of catalyst. The data are indicated in Table 6.

Example 4

Catalyst CAT-C supported on $Al_2O_3$ of the type C characterized by the following morphological parameters: gamma crystalline phase, surface area equal to 192 m$^2$/g, specific pore volume of 0.48 cm$^3$/g, average particle distribution of 165 μm.

The catalytic activity data are indicated in Table 7.

Example 5 Comparative 5

Catalyst CAT-D supported on $Al_2O_3$ of the type D characterized by the following morphological parameters: gamma crystalline phase, surface area equal to 120 m$^2$/g, specific pore volume of 0.25 cm$^3$/g, average particle distribution of 165 μm.

The catalytic activity data are indicated in Table 8.

Example 6

Catalyst CAT-E supported on $Al_2O_3$ of the type E characterized by the following morphological parameters: gamma crystalline phase, surface area equal to 205 m$^2$/g, specific pore volume of 0.53 cm$^3$/g, average particle distribution of 165 μm, presence of 1.5% by weight of $SiO_2$.

The catalytic activity tests are characterized by the use of a catalyst supported on an alumina containing 1.5% by weight of $SiO_2$. The catalytic activity data are indicated in Table 9.

Example 7

Effect of the Catalyst Particle Dimension on the Liquid-solid Separation

It is known that with an increase in the particle diameter it is easier and more economic to separate a solid from a liquid.

Figure 2:
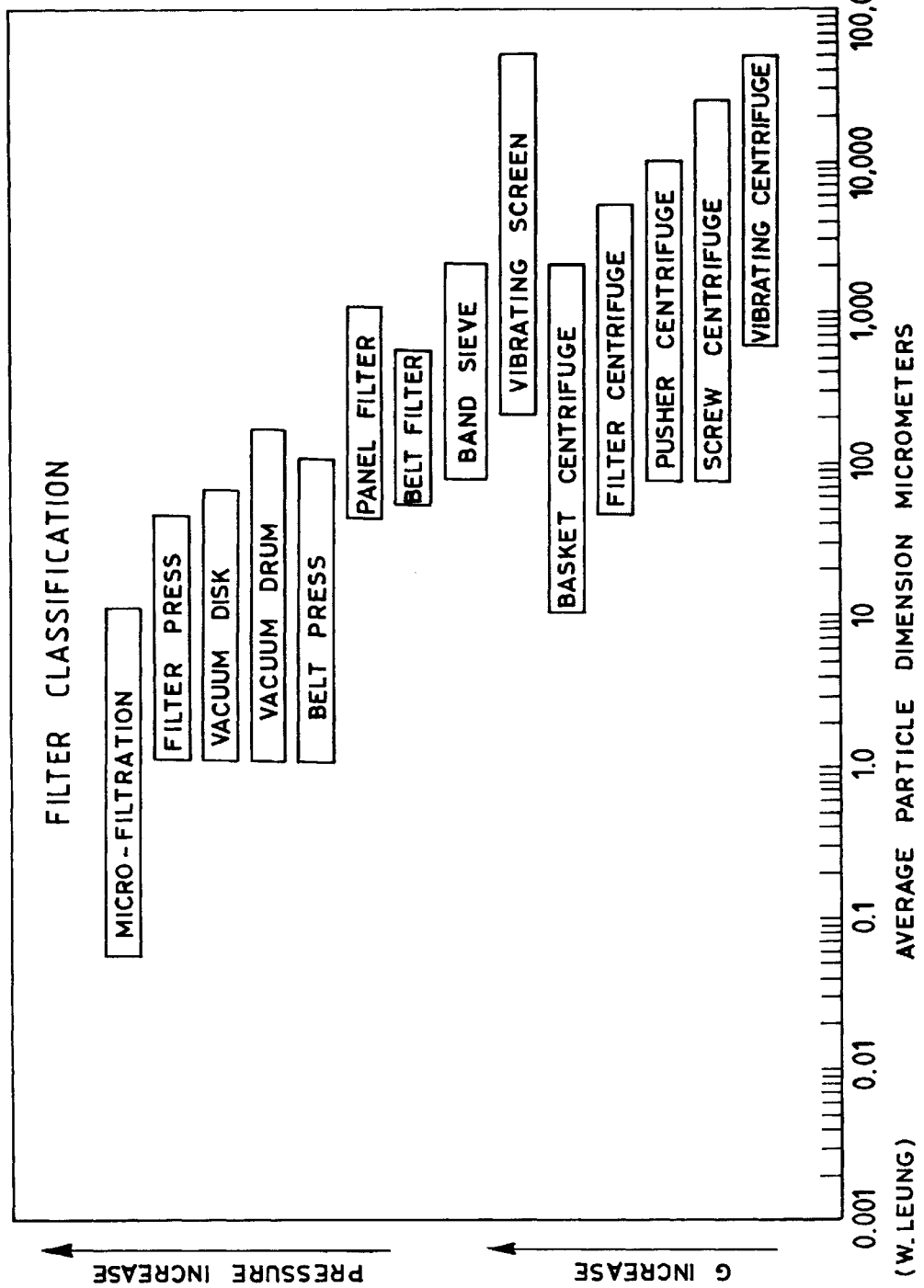

FIG. 1 (taken from W. Leung, Industrial Centrifugation Technology, McGraw-Hill Inc., March 1998), shows a classification of solid-liquid separation equipment, of the wall solid type, in relation to the particle size. The equipment is classified according to two different functioning principles: dynamic decanting (in which the acceleration induced on the particles is important) and static decanting (in which the surface characteristic of the decanter is important). From FIG. 1 it can be observed that, with an increase in the particle dimension, the required gravitational acceleration (R number) or required surface, decreases respectively. Decreasing the R number means reducing the rotation rate and therefore saving energy. Decreasing the surface means reducing the dimension of the apparatus. FIG. 2 (taken from W. Leung, Industrial Centrifugation Technology, McGraw-Hill Inc., March 1998) shows a classification of solid-liquid separation equipment, of the filtration type, in relation to the particle size. The equipment is classified according to two different functioning principles: filtration under pressure (in which the pressure difference exerted between upstream and downstream of the filter, is important) and filtrating centrifugation (in which the acceleration induced on the particles is important). From FIG. 2 it can be seen that, with an increase in the particle dimension, there is a decrease in the pressure required or gravitational acceleration required (R number), respectively. Decreasing the pressure, or the R number, means reducing the work required and therefore saving energy.

Figure 3:
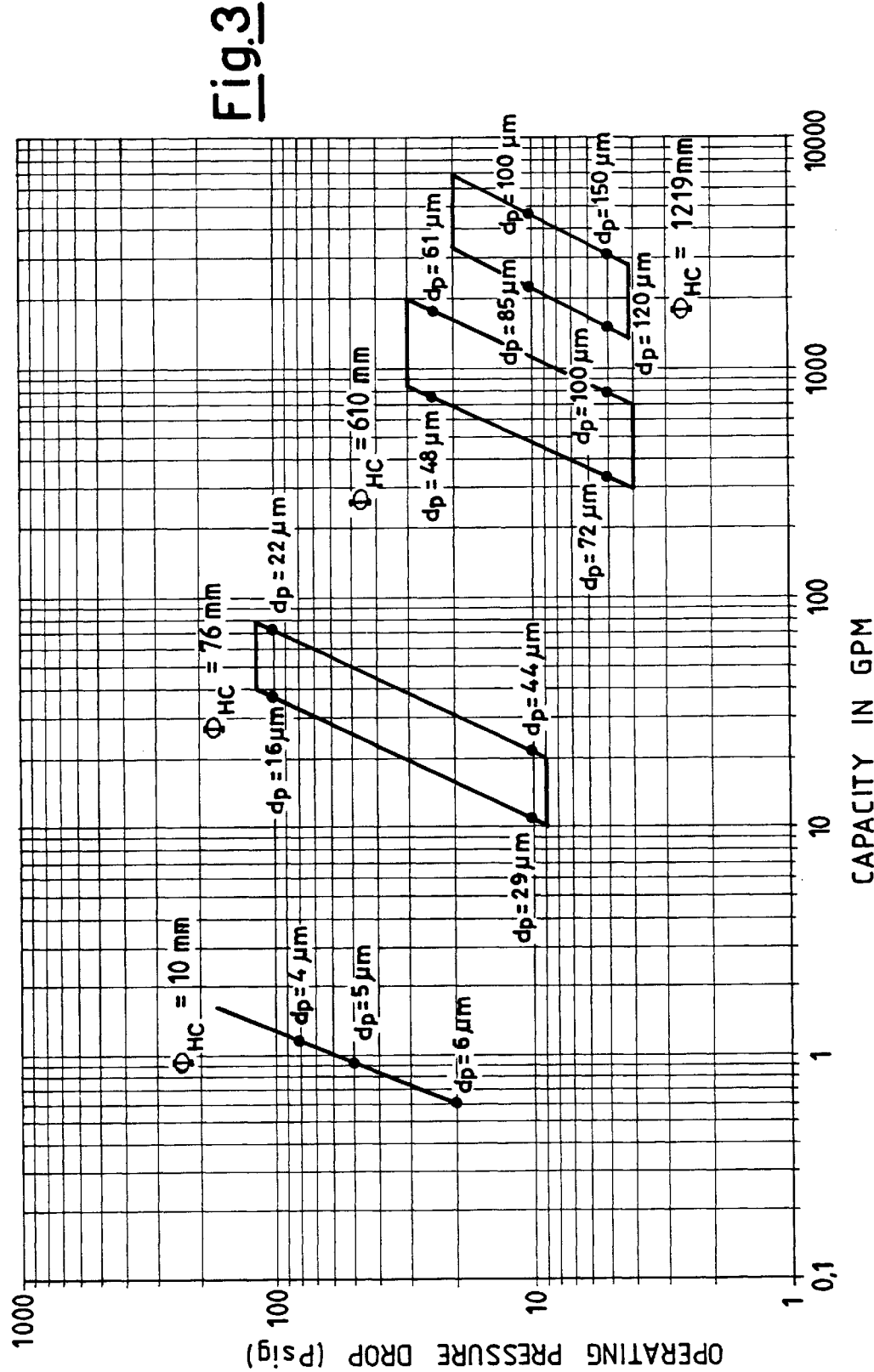

FIG. 3 (taken from a commercial publication of Dorr-Oliver, The DorrClone Hydrocyclone, Bulletin DC-2, 1989) shows the utilization ranges of commercial hydrocyclones in different dimensions as a function of the RPM capacity, the loss in operating pressure and particle dimension. A hydrocyclone is a static apparatus which exploits the difference in density between solid and liquid and the centrifugal force induced, to separate solid particles from the fluid in which they are suspended. With reference to a capacity of 680 $m^3/h$ of solid-liquid suspension to be treated, equal to about 3000 RPM (specific gravity of the solid 2.7, concentration of solid: 25% by weight, and separation efficiency: 95%), it can be observed that on increasing the particle size of the solid particles, it is possible to use a lower number of hydrocyclones, but with a greater diameter, according to Table 10:

TABLE 10

| Particle diameter | Hydrocycl. diameter | Total capacity/ single hydroycl.capacity | Nr. hydrocycl. required | Pressure drop (psig) |
|---|---|---|---|---|
| 5 $\mu$m | 10 mm | 3000/0.9 | 3333 | 40 |
| 44 $\mu$m | 3 inches (76 mm) | 3000/20 | 150 | 10 |
| 100 $\mu$m | 24 inches (610 mm) | 3000/700 | 4 | 5 |
| 150 $\mu$m | 48 inches (1219 mm) | 3000/3000 | 1 | 5 |

From Table 10 above it can be clearly seen that on passing from solid particles of 5 $\mu$m to particles of 150 $\mu$m, the number of hydrocyclones passes from 3000 to 1. This allows an enormous cost reduction for two reasons: the first is that the number of hydrocyclones required is reduced, the second is that the constructive difficulty, which increases with a decrease in the diameter of the hydrocyclone, is reduced.

Considerations on Example 7

Example 7, described above, has the purpose of demonstrating that:

As, in order to favor the liquid/solid separation unit, it is preferable to operate with solid particles having a larger average diameter, for example greater than 100 $\mu$m (in fact, with an increase in the particle diameter with the same concentration of solid, the volume required by the separation step and also the constructive difficulty are reduced), with catalysts not included in the scope of the present invention, it would no longer be possible to operate without internal diffusion control limitations. The use of a catalyst supported on particles with morphological characteristics identified in the present invention, allows a reduction in the separation weight without jeopardizing the effectiveness of the catalyst.

Discussion on Examples 1–6

The use of a catalyst supported on particles based on alumina with an average diameter ranging from 70 to 250 $\mu$m, a surface area higher than 175 $m^2/g$, a porous volume higher than 0.35 $cm^3/g$, allows catalytic performances to be obtained which are comparable to, if not higher than those obtained with analogous catalysts consisting of an alumina carrier having lower average particle dimensions, thus potentially less affected by morphological problems outside the above range.

Example 4 demonstrates how, with CAT-C, characterized by a carrier having morphological parameters (average particle dimension of 165 $\mu$m, a surface area of 192 $m^2/g$, a specific pore volume of 0.48 $cm^3/g$) within the range of the present invention, higher CoTY values are obtained (Table 7, test -a-) than those with comparative catalyst CAT-A (Table 4, test -a-) under analogous reaction conditions. Surprisingly with CAT-C, the selectivity to $CH_4$ is lower than the case described in the comparative example: $CH_4$ (%C)=8.90 for CAT-C and $CH_4$ (%C)=10.32 for CAT-A, whereas the productivity to $C_{5+}$ liquids is higher: $ProdC_{5+}$= 203 g/h/$kg_{cat}$ for CAT-C and $ProdC_{5+}$=151 g/h/$kg_{cat}$ for CAT-A. This clearly indicates that CAT-C of the present invention favors the formation of hydrocarbon products with a higher molecular weight, thus providing a further advantage for product transformation processes of the Fischer-Tropsch synthesis (e.g. hydroisomerization, hydrocracking). The selectivity to methane moreover can be further limited by slightly lowering the $H_2$/CO ratio in the feeding, as test -b- in Table 7 demonstrates. To obtain analogous CoTY levels, it is necessary to raise the temperature of comparative catalyst A to 235° C. (see Table 4, test -b-, compared to Table 7). These conditions however, even though producing an increased conversion of the reagents and therefore of CoTY, do not favor the selectivity to methane and the productivity to liquids.

Example 5 (Table 8) demonstrates how the use of alumina carriers with an average particle diameter of 165 $\mu$m is not effective when the other morphological parameters are outside the range indicated by the present invention. In fact, with comparative catalyst CAT-D, the catalytic performances are much lower than the case represented by example 4 (CAT-C). The CoTY values do not exceed 3.7 $h^{-1}$ with a productivity to $C_{2+}$ and $C_{5+}$ of about 110 and 75 g/h/$kg_{cat}$, respectively, i.e. of 43% and 37% respectively of the productivity obtained with the catalyst CAT-D.

Examples 2 and 3 indicated in Table 5 and 6 represent two different experimental tests carried out with comparative catalyst CAT-B, characterized by a carrier consisting of particles having an average diameter equal to 65 $\mu$m, a surface area of 175 $m^2/g$ and a specific pore volume of 0.43 $cm^3/g$. The catalytic performances obtained with this catalyst are still lower than those obtained with the catalyst supported on alumina C (CAT-C). More specifically, the case which is representative of the present invention proves to be more active (CoTY>7.0 $h^{-1}$) even if higher space velocities (GHSV) are adopted.

Example 6 (Table 9) relates to the catalytic test carried out with the catalyst CAT-E, representative of the present invention and obtained by deposition of cobalt on a carrier consisting of 98.5% by weight of $\gamma$-$Al_2O_3$ and 1.5% by weight of $SiO_2$. The CoTY of 6.2 $h^{-1}$ obtained with a GHSV equal to 1.85 $h^{-1}$ indicates a higher activity in terms of hourly molar conversion per mole of Co with respect to CAT-B. In fact, the CoTY values obtained with CAT-B at lower space velocities (Tables 5 and 6), CoTY=5.2 $h^{-1}$ for GHSV=1.35 $h^{-1}$ and CoTY=4.2 $h^{-1}$ for GHSV=1.5 $h^{-1}$, indicate the fact that the CoTY decreases with an increase in the space velocity. As far as the selectivities to methane are concerned, values of about 8%C are obtained with CAT-E.

TABLE 4

Comparative catalyst CAT-A

| TEST | a | b |
|---|---|---|
| Carrier | A | A |
| Surface area (m²/g) | 170 | 170 |
| Specific pore volume (cm³/g) | 0.43 | 0.43 |
| Average particle distribution (μm) | 60 | 60 |
| Quantity of catalyst (g) | 46.80 | 46.50 |
| GHSV (Nl/$g_{cat}$/h) | 2.35 | 2.35 |
| Temperature (° C.) | 230 | 235 |
| Test pressure (abs. bar) | 21 | 21 |
| Actual $H_2$/CO | 2.00 | 2.00 |
| CO conversion (%) | 48.3 | 55.0 |
| $H_2$ conversion (%) | 54.4 | 58.6 |
| CoTY (moles CO conv/h/moles Co) | 6.9 | 7.9 |
| Average $H_2O$ production (g/h/kg cat) | 294.16 | 330.54 |
| Selectivity $CH_4$ (% carbon) | 10.32 | 12.56 |
| Productivity $C_{2+}$ ($gC_{2+}$/h/$kg_{cat}$) | 208.95 | 236.28 |
| Productivity $C_{5+}$ ($gC_{5+}$/h/$kg_{cat}$) | 150.55 | 176.88 |

TABLE 5

Comparative catalyst CAT-B

| TEST | a | b |
|---|---|---|
| Carrier | B | B |
| Surface area (m²/g) | 175 | 175 |
| Specific pore volume (cm³/g) | 0.35 | 0.35 |
| Average particle distribution (μm) | 65 | 65 |
| Quantity of catalyst (g) | 64.70 | 64.70 |
| GHSV (Nl/$g_{cat}$/h) | 1.50 | 1.50 |
| Temperature (° C.) | 230 | 230 |
| Test pressure (abs. bar) | 21 | 21 |
| Actual $H_2$/CO | 2.25 | 1.65 |
| CO conversion (%) | 50.8 | 43.8 |
| $H_2$ conversion (%) | 51.6 | 45.9 |
| CoTY (moles CO conv/h/moles Co) | 4.2 | 4.2 |
| Average $H_2O$ production (g/h/kg cat) | 198.09 | 159.13 |
| Selectivity $CH_4$ (% carbon) | 10.58 | 9.53 |
| Productivity $C_{2+}$ ($gC_{2+}$/h/$kg_{cat}$) | 136.39 | 116.17 |
| Productivity $C_{5+}$ ($gC_{5+}$/h/$kg_{cat}$) | 105.87 | 92.93 |

TABLE 6

Comparative catalyst CAT-B

| TEST | a | b |
|---|---|---|
| Carrier | B | B |
| Surface area (m²/g) | 175 | 175 |
| Specific pore volume (cm³/g) | 0.35 | 0.35 |
| Average particle distribution (μm) | 65 | 65 |
| Quantity of catalyst (g) | 73.00 | 73.00 |
| GHSV (Nl/$g_{cat}$/h) | 1.35 | 1.35 |
| Temperature (° C.) | 230 | 230 |
| Test pressure (abs. bar) | 21 | 21 |
| Actual $H_2$/CO | 2.00 | 2.07 |
| CO conversion (%) | 61.2 | 59.4 |
| $H_2$ conversion (%) | 61.3 | 59.8 |
| CoTY (moles CO conv/h/moles Co) | 5.2 | 4.9 |
| Average $H_2O$ production (g/h/kg cat) | 222.83 | 201.52 |
| Selectivity $CH_4$ (% carbon) | 8.64 | 9.66 |
| Productivity $C_{2+}$ ($gC_{2+}$/h/$kg_{cat}$) | 164.01 | 142.47 |
| Productivity $C_{5+}$ ($gC_{5+}$/h/$kg_{cat}$) | 140.24 | 118.37 |

TABLE 7

Catalyst CAT-C

| TEST | a | b |
|---|---|---|
| Carrier | C | C |
| Surface area (m²/g) | 192 | 192 |
| Specific pore volume (cm³/g) | 0.48 | 0.48 |
| Average particle distribution (μm) | 165 | 165 |
| Quantity of catalyst (g) | 43.50 | 43.50 |
| GHSV (Nl/$g_{cat}$/h) | 2.35 | 2.35 |
| Temperature (° C.) | 230 | 230 |
| Test pressure (abs. bar) | 21 | 21 |
| Actual $H_2$/CO | 2.00 | 1.92 |
| CO conversion (%) | 45.0 | 46.6 |
| $H_2$ conversion (%) | 47.0 | 47.0 |
| CoTY (moles Co conv/h/moles Co) | 7.2 | 7.3 |
| Average $H_2O$ production (g/h/kg cat) | 353.33 | 279.02 |
| Selectivity $CH_4$ (% carbon) | 8.90 | 7.77 |
| Productivity $C_{2+}$ ($gC_{2+}$/h/$kg_{cat}$) | 255.95 | 241.99 |
| Productivity $C_{5+}$ ($gC_{5+}$/h/$kg_{cat}$) | 203.23 | 189.94 |

TABLE 8

Comparative catalyst CAT-D

| TEST | a | b |
|---|---|---|
| Carrier | D | D |
| Surface area (m²/g) | 120 | 120 |
| Specific pore volume (cm³/g) | 0.25 | 0.25 |
| Average particle distribution (μm) | 165 | 165 |
| Quantity of catalyst (g) | 42.30 | 42.30 |
| GHSV (Nl/$g_{cat}$/h) | 2.35 | 2.35 |
| Temperature (° C.) | 230 | 230 |
| Test pressure (abs. bar) | 21 | 21 |
| Actual $H_2$/CO | 2.00 | 1.95 |
| CO conversion (%) | 24.0 | 24.7 |
| $H_2$ conversion (%) | 27.6 | 28.6 |
| CoTY (moles CO conv/h/moles Co) | 3.6 | 3.7 |
| Average $H_2O$ production (g/h/kg cat) | 153.90 | 161.47 |
| Selectivity $CH_4$ (% carbon) | 11.09 | 10.88 |
| Productivity $C_{2+}$ ($gC_{2+}$/h/$kg_{cat}$) | 109.16 | 113.82 |
| Productivity $C_{5+}$ ($gC_{5+}$/h/$kg_{cat}$) | 72.30 | 76.93 |

TABLE 9

Catalyst CAT-E

| TEST | a | b |
|---|---|---|
| Carrier | E | E |
| Surface area (m²/g) | 205 | 205 |
| Specific pore volume (cm³/g) | 0.53 | 0.53 |
| Average particle distribution (μm) | 165 | 165 |
| Quantity of catalyst (g) | 54.40 | 54.70 |
| GHSV (Nl/$g_{cat}$/h) | 1.85 | 1.85 |
| Temperature (° C.) | 230 | 230 |
| Test pressure (abs. bar) | 21 | 21 |
| Actual $H_2$/CO | 2.00 | 1.95 |
| CO conversion (%) | 53.2 | 54.3 |
| $H_2$ conversion (%) | 58.4 | 59.5 |
| CoTY (moles CO conv/h/moles Co) | 6.2 | 6.3 |
| Average $H_2O$ production (g/h/kg cat) | 251.65 | 250.27 |
| Selectivity $CH_4$ (% carbon) | 8.07 | 7.93 |
| Productivity $C_{2+}$ ($gC_{2+}$/h/$kg_{cat}$) | 194.96 | 207.47 |
| Productivity $C_{5+}$ ($gC_{5+}$/h/$kg_{cat}$) | 161.92 | 175.73 |

What is claimed is:

1. A supported cobalt-based catalyst, comprising a catalytically active phase supported on a carrier consisting of greater than 80% by weight of aluminum oxide and having an average particle diameter, measured by Coulter LS230, ranging from 120 to 180 μm, a surface area greater than 175

$m^2/g$ and a pore volume greater than 0.35 $cm^3/g$, measured by the BET method.

2. The catalyst according to claim 1, wherein the catalyst has a pore volume greater than 0.40 $cm^3/g$.

3. The catalyst according to claim 1, wherein the catalyst has a surface area ranging from 185 $m^2/g$ to 210 $m^2/g$.

4. The catalyst according to claim 1, wherein the catalytically active phase of the catalyst consists of greater than 80% by weight of cobalt.

5. The catalyst according to claim 4, wherein the catalytically active phase of the catalyst contains a promoter selected from the group consisting of K, Na, Mg, Sr, Cu, Mo, Ta, W and metals of Group VIII of the Periodic Table.

6. The catalyst according to claim 1, wherein said carrier contains a structural stability promoter selected from the group consisting of Si, Zr, Ta, Zn, Sn, Mn, Ba, Ca, La and Ce.

* * * * *